(12) United States Patent
Jernigan

(10) Patent No.: US 8,622,904 B2
(45) Date of Patent: Jan. 7, 2014

(54) USE OF HEAT SENSITIVE COLOR CHANGING FORMULA TO DETECT AND PREVENT THE ONSET OF DECUBITUS ULCERS

(76) Inventor: Lisa Jernigan, Pensacola, FL (US)

( * ) Notice: Subject to any disclaimer, the term of this patent is extended or adjusted under 35 U.S.C. 154(b) by 418 days.

(21) Appl. No.: 12/845,425

(22) Filed: Jul. 28, 2010

(65) Prior Publication Data

US 2011/0028804 A1 Feb. 3, 2011

Related U.S. Application Data

(60) Provisional application No. 61/228,987, filed on Jul. 28, 2009.

(51) Int. Cl.
*A61B 5/00* (2006.01)
(52) U.S. Cl.
USPC .......................................................... 600/306
(58) Field of Classification Search
USPC ................................................. 600/306, 592
See application file for complete search history.

(56) References Cited

U.S. PATENT DOCUMENTS

| | | | |
|---|---|---|---|
| 4,305,961 A | 12/1981 | Tsutsumi et al. | |
| 4,394,447 A | 7/1983 | Cadmus et al. | |
| 4,515,700 A | 5/1985 | Hitzman | |
| 5,198,469 A | 3/1993 | Sakata | |
| 5,911,981 A | 6/1999 | Dahms et al. | |
| 5,955,406 A | 9/1999 | Dubief et al. | |
| 5,993,793 A | 11/1999 | Simone et al. | |
| 6,001,344 A | 12/1999 | Villa et al. | |
| 6,328,910 B1 * | 12/2001 | Askill et al. | ............... 252/299.7 |
| 2008/0166303 A1 * | 7/2008 | Tamarkin et al. | ............... 424/43 |
| 2008/0214962 A1 * | 9/2008 | Kantro et al. | .................. 600/592 |

OTHER PUBLICATIONS

Skin Safety Protocol: Risk Assessment and Prevention of Pressure Ulcers. Mar. 2007. Institute for Clinical Systems Improvement. p. 16.*
Bain, Duncan, Wain, Greg and Ferguson-Pell, Martin, "A Device for Early Identification of Pressure Ulcers," Centre for Disability Research and Innovation, University College London, European Pressure Ulcer Advisory Panel, http://www.epuap.org/review5_1/page5d.html.
Balla, A., Romanin, A., and Rota, P., "The Use of Cholesteric Liquid Crystals in the Study of Skin Temperature and Their Applications in Aviation Medic," Rivista di Medicina Aeronautica e Spaziale, 35, Jan-June, 51-61 (in Italian), EEVL Engineering Section, Liquid Crystal Database, http://www.eevl.ac.uk/lcd/index.htm.
US 6,290,977, 09/2001, Friars et al. (withdrawn).
Binnemans, Koen, "Liquid Crystals," Chemistry Encyclopedia, Chemistry Explained, Foundations and Applications, http://www.chemistryexplained.com/Kr-Ma/Liquid-Crystals.html.

(Continued)

*Primary Examiner* — Navin Natnithithadha
*Assistant Examiner* — Etsub Berhanu
(74) *Attorney, Agent, or Firm* — Phillip E. Walker; Waddey Patterson

(57) ABSTRACT

A method for diagnosing the onset of necrosis, decubiti, and/or decubitus ulcers in the skin of a patient. Included is a topical product accessed in liquid form and applied to the skin. The product displays thermochromic temperature change when the product comes into contact with human skin tissue to identify body parts at risk for tissue necrosis by the color differences.

17 Claims, 3 Drawing Sheets

(56) References Cited

OTHER PUBLICATIONS

Birke, James A. (Jim), (Responding to Invited Commentary Response on Armstrong, David G., Lavery, Lawrence A., Liswood, Paul J., Todd, William F., Tredwell, Jeffrey A., "Infrared Dermal Thermometry for the High-Risk Diabetic Foot," Physical Therapy, vol. 77, No. 2, Feb. 1997), http://www.thefreelibrary.com 1997.

Cho, M.H., Cho, C.Y.L., Cho, C., Cho, A. and Cho, L., "Liquid Crystal Thermography to Show Two Way Nerve Reflex Pathways Between the Corresponding Point Body and the Ear," Fed. Amer. Soc. Exper. Biol., 62nd Ann. Meet., Atlantic City, Apr. 9-14, 1978, 398, EEVL/ Engineering Section/Liquid Crystal Database, http://www.eevl.ac.uk/lcd/index.htm.

Color Change Corporation, "Leuco Dyes," (Thermocromic Leuco Dyes) Color Change Corporation 2002, Color Change Corporation, 1545 Burgundy Parkway, Streamwood, IL 60107, http://www.colorchange.com/Leuco%20Dyes%204.htm.

Color Change Corporation, "Liquid Crystals," http://www.colorchange.com/Liquid% 20Crystal.htm.

Corkery, Robert W., "A Variation on Luzzati's Soap Phases. Room Temperature Thermotropic Liquid Crystals," Phys. Chem. Chem. Phys., 2004, 6 (7), 1534-1546, DOI: 10, 1039/b315595c, http://www.rsc.org/CFmuscat/intermediate_abstract.cfm?FURL=/ej/CP/2004/b315595c/b3.

Davenport, C.J., "A Technique for Measuring Local Heat Transfer Due to an Impinging Liquid Spray," ASME Proc. 1989 Nat. Heat Transfer Conf., Philadelphia, Pa., Aug. 6-9, 1989, HTD 106, 531-536, http://www.eevl.ac.uk/lcd/index.htm.

Davison, T.W., "High Resolution Liquid Crystal Thermography in Medicine and Physiology," Seminar on Photographic Sci. and Eng. in Medicine Equip, Article No. 282, Newton Mass., Ju 20-21, 1972, 14-15, EEVL, Engineering Section, Liquid Crystal Database, http://www.eevl.ac.uk/lcd/index.htm.

Demus, D., Gloza, A. and Weissflog, W., "Cholesteric Liquid Crystal Mixtures for Thermography Comprising Cholesteryl Ester(s) and Cholesteryl cl-" German Patent DD 156639, Sep. 8 1982 (in German).

Dribbon, B.S., "Application and Value of Liquid Crystal Thermography," J. Amer. Podiatry Assoc., 73(B), 400-404, 1983, EEVL/Engineering Section/Liquid Crystal Database, http://www.eevl.ac.uk/lcd/index.htm.

Gordon, William L., Koenig, Jack L., and Cramer, Peter G., Case Western Reserve University and Kent State University, The PLC Project, "Cholesteric Phases," Phases of Liquid Crystals, Polymers and Liquid Crystals Teams (1994-2004), plc.cwru.edu/tutorial/enhanced/files/lc/phase/phase.htm.

Hanson, P, Plaghki, L. and De Nayer, J., "Liquid Crystal Thermography in the Evaluation of Chronic Sciatica," Ann. Readapt. Med. Phys., 1987, Phys., 30(4), 423-431 (In French), EEVL/ Engineering Section/ Liquid Crystal Database, http://www.eevl.ac.uk/lcd/index.htm.

Hosie, K.B., Wardrope, J., Crosby, A.C., and Ferguson, D.G., "Liguid Crystal Thermography in the Diagnosis of Scaphoid Fractures," Arch. Emergency Mediine, 1987, 4, 117-120, EEVL/Engineering Section/Liquid Crystal Database, Article No. 113, http://www.eevl.ac.uk/lcd/indes.htm.

Jain, G.L., Guha, S.K. and Pasricha, J.S., "A Pressure Indicating Ring for Patients With Hand Pressure Sense Loss," IEEE/Engineering in Medicine and Biology Soc. Ann. Conf., New Orleans, Nov. 4-7, 1988, IV, 1597-1598, http://www.eevl.ac.uk/lcd/index.htm.

Jones, Michael I., Marini, Irmo, Slate, John R., "Prevention Practice Differences Among Persons With Spinal Cord Injuries Who Rarely Versus Frequently Sustain Pressure Ulcers," Rehabilitation Counseling Bulletin, Hammill Institute on Disabilities, Rehabil Couns Bull Apr. 2005 vol. 48 No. 3 139-145.

Kalodiki, E., Calahoras, L., Geroulakos, G. and Nicolaides, A.N., "Liquid Crystal Thermography and Duplex in the Preoperative Marking of Baricose Veins," Phlebology, 1995, 10, 110-114, EEVL/ Engineering Section/Liquid Crystal Database, Article No. 839, http://www.eevl.ac.uk/lcd/index.htm.

Kosiak, Michael, M.D., "Prevention and Rehabilitation of Pressure Ulcers," Advances In Skin & Wound Care, May 1991, vol. 4, Issue 2, Lippincott Williams & Wikins.

Lenz, U. and Schmidt, P., "Use of Cholesteric Liquid Crystal Thermography for Diagnosing Radiation Injuries of Human Skin," NTIS SAAS-232 (In German) 1978, Article No. 85, EEVL Engineering Section, Liquid Crystal Database, http://www.eevl.ac.uk/lcd/index.htm.

Nelson, J., "Implement for Measuring Skin Temperatures," U.S. Patent 4,437,471, Mar. 20, 1984, http://www.eevl.ac.uk/lcd/index.htm.

Nishimura, T., Fujiwara, M. and Miyashita, H., "Visualization of Temperature Fields of Transient Natural Convection With Maximum Density Effect in a Water-Filled Enclosure by Chiral Nematic Liquid Crystals," J. Chem. Eng. Japan, 1990, vol. 23(2), 241-244, EEVL, Engineering Section, Liquid Crystal Database, http://www.eevl.ac.uk/lcd/index.htm.

Panigrahi, P.K., "Colourful World of Liquid Crystals," Technology, vol. 3 No. 2, Mar. 2000, Department of Mechanical Engineering, Indian Institute of Technology Kanpur, http://www.iitk.ac.in/infocell/Archive/dirmar2/techno_crystals.html.

Pochaczevsky, R., Pillari, G. and Feldman, F., "Liquid Crystal Contact Thermography of Deep Venous Thrombosis," Am. J. Roentgenol., 1982, 138(4), 717-723, Article No. 306, EEVL/Engineering Section/Liquid Crystal Database, http://www.eevl.ac.uk/lcd/index.htm.

Pochaczevsky, R., Wexler, C. E., Meyers, P.H., Epstein, J.A., et al., "Liquid Crystal Thermography of the Spine and Extremities," J. Neurosurg., 1982, 56(3), 386-395, EEVL/ Engineering Section/ Liquid Crystal Database, http://www.eevl.ac.uk/lcd/index.htm.

Ring, E.F.J., "Skin Temperature Measurement," Bioeng. Skin, 1986, 2, 15-30, Article No. 287, EEVL Engineering Section, Liquid Crystal Database, http://www.eevl.ac.uk/lcd/index.htm.

Sabourin, L.M., "Non destructive Testing of Bonded Structures With Liquid Crystals," Bonding Conf., Mar. 14, 1966. NTIS N66-34137, NASA Marshall Space Flight Center, Structural Adhesive, Article No. 449, EEVL/ Engineering Section/Liquid Crystal Database, http://www.eevl.ac.uk/lcd/index.htm.

Savvov, A., "Liquid Crystal Developments for Medicine," NTIS N79-21745, 1979, EEVL/Engineering Section / Liquid Crystal Database, http://www.eevl.ac.uk/lcd/index.htm.

Shakhashinii, Prof., "Liquid Crystals," Chemical of the Week, Chemistry 103-1, Nov. 28, 2007, www.scifun.org.

Tyson, Jeff, "How LCDs Work," "Nematic Phase Liquid Crystals," Jul. 17, 2000. HowStuffWorks.com., http://electronics.howstuffworks.com/lcd.htm, Nov. 8, 2010.

\* cited by examiner

USE OF HEAT SENSITIVE COLOR CHANGING FORMULA TO DETECT AND PREVENT THE ONSET OF DECUBITUS ULCERS

CROSS-REFERENCES TO RELATED APPLICATIONS

This application is a non-provisional of, and claims priority to, U.S. Patent Application Ser. No. 61/228,987 filed Jul. 28, 2009 entitled "Use of Heat Sensitive Color Changing Formula to Detect and Prevent the Onset of Decubitus Ulcers", which is hereby incorporated by reference in its entirety.

I, Lisa Jernigan, residing at 825 Fleming Court Pensacola, Fla. 32514, have invented a new and useful "Use of Heat Sensitive Color Changing Formula to Detect and Prevent the Onset of Decubitus Ulcers."

A portion of the disclosure of this patent document contains material that is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

All patents and publications described or discussed herein are hereby incorporated by reference in their entirety.

BACKGROUND OF THE INVENTION

The present invention relates generally to the detection of subcutaneous necrosis in order to prevent or arrest development of decubitus ulcers. More specifically, the present invention relates generally to a product that exhibits thermochromic color changes in response to temperature fluctuations on the body to detect the onset of conditions favorable to decubitus ulcers.

Thermochromism is one type of process by which a reversible change in the color of a compound is induced by stimuli. In thermochromism, the stimulus is a change in temperature. Liquid crystals and leuco dyes are the two basic types of compounds typically used in thermochromism. The typical characteristics of liquid crystals include a limited range within which the color can fluctuate supported by a substantially precise response to subtle temperature changes. Leuco dyes have a less accurate response to a temperature fluctuation, but allow a wider range of colors in their application.

As such, depending on the application, liquid crystals or leuco dyes can be used to view a change in the color of a compound induced by a temperature change. For example, leuco dyes are typically used in applications wherein temperature response accuracy is not critical and the subtleties in color change can be overlooked. Conversely, liquid crystals typically are used in applications where the change in temperature and the corresponding change in color can be accurately defined and the application to which they are used require some type of definiteness. As such, liquid crystals are known to have some medical applications including the evaluation of complex pain states associated with arthritis, soft tissue injuries, back pain diseases, and damage to the nervous system.

However, there are difficulties with the use of liquid crystal material in medical applications. Namely, it has been documented that it is difficult to quantify the visual data and correlate that to a prediction of a medical state. It is this quantification, generally related to or dependent on visible recognition, which can be extremely susceptible to observer bias and can lead to improper use or interpretation. A review of liquid crystal technology can be found in "Colourful World Of Liquid Crystals" in the March, 2000 issue of *Technology*, Volume 3, No. 2.

Additionally, reversible thermochromic materials have been used in personal care products. For example, U.S. Pat. No. 6,290,977, which has since been withdrawn, discloses topical flowable personal care products, and more specifically, a shower gel shampoo, body lotion, moisturizing cream, sunscreen, skin toner, or the like, that exhibits thermochromic color changes in response to body heat or the heat of a bath or shower.

Other studies have directed efforts at infrared skin temperature evaluation in the protection and treatment of ulcers. Namely, a study by Jim Birke titled "Infrared Thermal Thermometry for the High Risk Diabetic Foot" as appearing Feb. 1, 1997 in *Physical Therapy*, discloses the use of a hand held infrared skin temperature probe to record the differences in skin temperatures between various diabetic ailments. The study focused on predicting the affect of various diabetic ailments by studying both the affected foot and the non-affected foot on those diabetic patients.

Other medical research has been directed at decubitus ulcers, also known as pressure sores or bed sores or pressure ulcers. According to Linda Pershall, R.N., B.S.N., of the LDHP Medical Review Services Corp., decubitus ulcers are preventable and can range from a very mild pink coloration of the skin to a very deep wound extending to and sometimes through internal organs and into the bone. These ulcers are classified according to the severity of the wound and are usually in four stages or types.

The decubitus ulcers are generally formed from pressure or friction caused by pressure on the skin or friction between the skin and another object. The area of tissue that lies just over bone is susceptible to the formation of decubitus ulcers. In the case of pressure as the cause of these ulcers, immobility of a person, such as a debilitated person, is generally the cause. The weight of the person's body presses on the bone which in turn presses on the skin and tissue that cover that bone. That pressure traps the tissue between the bone structure and an outside object, such as a bed, chair or wheelchair and the like, and compresses the blood vessels in the skin and underlying tissues. This pressure causes the tissue to begin to decay from lack of blood circulation.

Additionally, reoccurring friction cause decubitus ulcers. For example, reoccurring movement that causes the skin to rub against an outside object, such as a bed, wheelchair, cast, brace and the like, can damage the small blood vessels and diminish the blood supply to a particular point.

Contributing factors to these ulcers are excess moisture, such as incontinence of the bowels and/or bladder or from perspiration. Additionally, general poor health, undernourishment, obesity, and diabetes can contribute to these ulcers. Poor hygiene and dehydration can also factor in the size and intensity of the ulcers.

The four classifications of the decubitus ulcer are four basic stages with stage one being the earlier mild stages and stage four being the most severe. Stage one represents the stage when the skin is still intact and shows signs of blanchable erythema from reactive hyperemia that typically can resolve itself within 24 hours with the relief of pressure. Increased temperature, such as warmth, and a warming of the skin, and induration is usually present. If the pressure continues, the erythema typically does not blanche with pressure and this can be the first outward sign of tissue destruction. Stage Two represents a partial thickness loss of skin involving the epidermis. This lesion may represent as an abrasion blister or superficial ulceration. Stage Three represents a full thickness loss of skin that extensions into subcutaneous tissue. This lesion appears as a crater that can include undermining of adjacent tissue. Stage four represents a full thickness loss of skin and subcutaneous with an extension into underlying fascia. Obviously it is ideal to detect these types of ulcers in Stage One.

From the inventor's experience as a registered nurse in acute and long-term care facilities and home health, a general theory developed that one explanation for the high rate of decubitus ulcers is poor skin assessment by caregivers. Inpatient facility staff is routinely burdened with an unmanageable number of patients, resulting in a critically limited amount of time per patient for the staff. Some staff may also be unskilled in skin assessments. At-home caregivers also appear to lack both the knowledge and skill to assess skin condition. Additionally, patients with hyper-pigmented skin often face a greater risk of lack of early detection of tissue necrosis because of the difficulty in visually assessing contrasts in skin color. In fact, in 2004, a study of patients in skilled nursing facilities showed a higher prevalence of decubiti in African American patients than white patients leading to the theory that the higher incidence is attributable, at least in part, to the challenge in assessing darker skin.

A cursory literature survey related to prevalence and costs of decubitus ulcers reveals that in the United States, alone, estimates for the occurrence of decubiti run as high as 4.5 million, annually; with up to 25% of that number occurring in the acute care setting. The estimated annual costs for treating decubiti range from $5 to $8.5 billion, excluding costs attributable to the settlement of negligence claims resulting from decubiti. Deaths directly related to decubiti total approximately sixty thousand annually. Again, these figures are for only the United States. Decubiti, however, are a world-wide problem.

According to Dr. Michael Kosiak in *Prevention and Rehabilitation of Pressure Ulcers* from WouldHEAL.com, 8/04, tissue necrosis can result after only 30-60 minutes of ischemia/pressure and repeated ischemic episodes have a cumulative effect on tissue. He further explains that the "earliest clinical evidence of damage to skin is . . . inflammation . . . which lasts for several hours after the pressure is relieved." He concludes that the "ability to recognize clinically the development of skin changes involving only the dermis, with its associated inflammatory response, is infinitely more important than (classifying advanced decubiti)."

As previously stated, based on the severity of tissue breakdown/depth of the wound, decubitus ulcers are categorized in four stages. Stage One is the earliest stage, with the most advanced stage, Stage Four, indicating full tissue necrosis and possible damage to muscle and/or bone. Obviously, the greater costs are associated with the more advanced stages. Therefore, one answer to reducing the incidence of the later stages and related costs is the detection of the earliest stage, Stage One. Authors in a study of decubiti in the UK stated, "The focus of attention should be on prevention (of decubiti)—prevention of initial tissue damage, prevention of progression of an ulcer to a more severe grade . . . ."

Current, commonly practiced prevention techniques include repositioning an immobile patient every two hours to reduce pressure on the same body part, use of airflow beds, and monitoring patients' nutrition. The problems with these methods are that turning and monitoring require strict consistency, which, based on statistical data of occurrence, is not present for most patients. The airflow beds are costly to both facilities and patients and are very limited in use. In one study of 30 patients who developed a total of 45 decubitus ulcers, eighteen were on turning schedules; seventeen had pressure-reducing devices on their beds. For that patient group, the average length of time from detection of the ulcer to healing, for those that did heal, was 116 days—nearly 4 months of treatment and expense and increased care from medical personnel.

What is needed then is a method and product to detect and prevent the onset of decubitus ulcers. This method and product would preferably react to the body and indicate the early stages of decubiti, while providing a readily apparent indication of the same. This needed method and product is lacking in the art.

BRIEF SUMMARY OF THE INVENTION

Disclosed herein is a topical product accessed in liquid form and applied to the skin. The product displays thermochromic temperature change when the product comes into contact with human skin tissue to identify body parts at risk for tissue necrosis by the color differences.

The product offers the opportunity for a major reduction in the incidence of decubiti, with the result of reducing related treatment and other costs by billions of dollars per year. A value in the current invention lies in the fact that that patients can avoid long-term suffering with early diagnosis by the current intervention and the associated early stage treatment and prevention of the same.

The extent of use of the invention can be far-reaching. The product has application in inpatient facilities (both acute and long-term care), in private homes, outpatient facilities, in the assessment and treatment of diabetic patients, patients suffering from peripheral neuropathy, venous stasis ulcers, or deep vein thrombosis, a routine part of any emergency medical kit in remote areas where frostbite is a concern, at chemical plants, and locations where a person is bedbound or has limited mobility for any length of time.

Also disclosed herein is a method of skin diagnosis of a patient. The method comprises providing a topical solution containing thermochromic material, applying that solution to the skin of the patient, recording the color of the solution as it appears on the skin of the patient, analyzing changes in the color of the solution as affected by the skin of the patient after a period of predetermined time, and correlating locations of changes in color of the solution to increase temperature of the skin at the color change location and to the onset of decubiti.

The method can also include using thermochromic material comprised of a plurality of liquid crystals or a leuco dye. The method can also further include providing a color key indicating the correlation between the solution color change and ranges of temperature of the skin proximate to the solution. The solution additionally can be in liquid form and can be applied as a spray. The predetermined time can be less than 10 seconds and can even be less than 5 seconds.

It is therefore a general object of the present disclosure to provide a method of identifying a risk for tissue necrosis.

Another object of the present disclosure is to provide a method for identifying the onset of decubitus ulcers and/or decubiti.

Another object of the present disclosure is to provide a method of identifying the onset of other ailments or illnesses that have a symptom of increased skin temperature.

Another object of the present disclosure is to provide a kit that assists in the early diagnosis of decubitus ulcers, decubiti, and/or tissue necrosis.

Other and further objects, features and advantages of the present invention will be readily apparent to those skilled in the art upon reading of the following disclosure when taken in conjunction with the accompanying drawings.

DETAILED DESCRIPTION OF THE INVENTION

Figure 1:
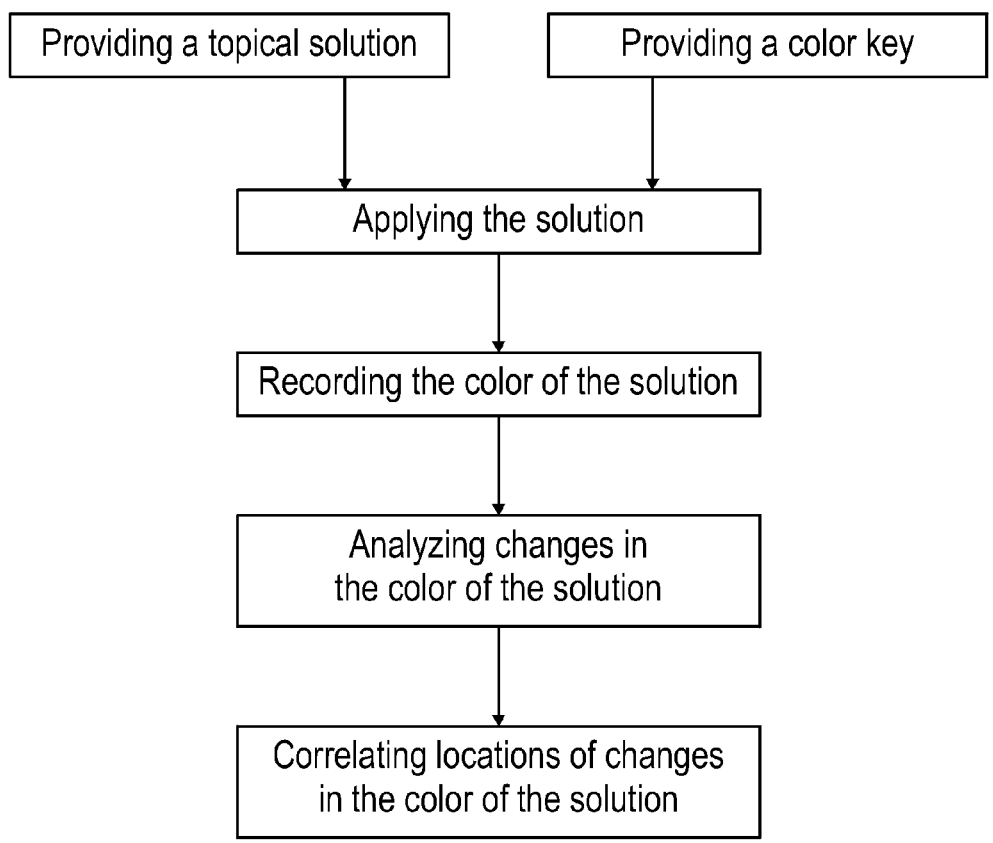
FIG. 1 shows a flowchart of an example of a methodology taught in accordance with the current disclosure.
Figure 2:
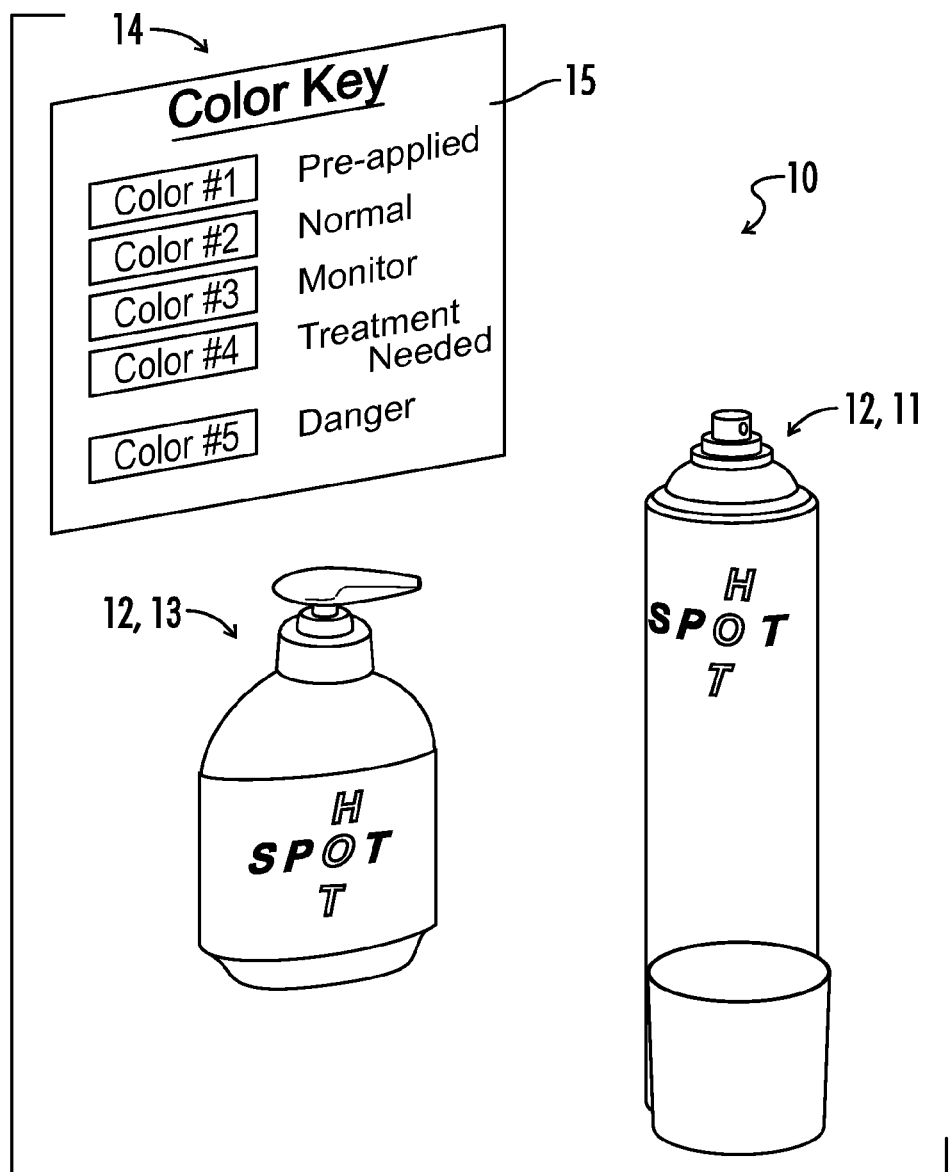
FIG. 2 is an example of a kit made in accordance with the current disclosure with an example of a potential color key or guide.

Disclosed herein is a topical product accessed in preferably liquid form and applied to the skin. The product displays thermochromic temperature changes when the product comes into contact with human skin tissue to identify body parts at risk for tissue necrosis by the color differences. The product can be applied through a spray or pump dispenser in various forms. For example, liquid soap, emollient, or water, and related products can be used. The product displays a thermochromic temperature change when product comes into contact with human skin in order to identify body part(s) at risk for tissue necrosis by the resulting color differences in product. Ideally the product can be washed off or rubbed into skin.

Also disclosed is a method for diagnosing the onset of decubitus ulcers in the skin of a patient. The method comprises providing a color key and a topical solution having a first color and containing thermochromic material. The color key indicates the correlation between the solution color and a ranges of temperatures of the solution as the solution reacts to temperature variances, including the variance in skin temperatures to which the solution can be applied.

The method further comprises applying the solution to the skin of the patient and recording the color of the solution as adjusted by variances in the temperature of the skin. The method also includes analyzing the changes in the color of the solution as affected by the skin of the patient after a period of predetermined time. The method further includes correlating the locations of changes in color of the solution to increase temperature of the skin at the color change location and further correlating that color change to the early stages of tissue necrosis, decubiti, and/or decubitus ulcers.

In a preferred embodiment the period of predetermined time is less than 10 seconds which allows for reaction and for interaction between the skin and the solution. In a more preferred embodiment the predetermined time is less than 5 seconds which decreases the length of time needed to analyze the color change. In a most preferred embodiment this period of predetermined time is approximately 1 second which further speeds up the analytical time for the determination of the onset of decubitus ulcers.

A kit 10 for the early diagnosis of tissue necrosis, decubiti, and/or decubitus ulcers is disclosed. The kit 10 includes an applicator 12 used to provide the solution in an acceptable form such as liquid, ointment, emollient, and the like. The applicator 12 can be an aerosol dispenser 11, a pump dispenser 13, or other dispensers known in the art to dispense such a solution. The kit includes a color key or guide 14 having various indicia 15 that correlate the colors seen on the solution with various temperatures and resulting potential issues with tissue necrosis, decubiti, and/or decubitus ulcers of the skin onto which the solution is applied.

Figure 3:
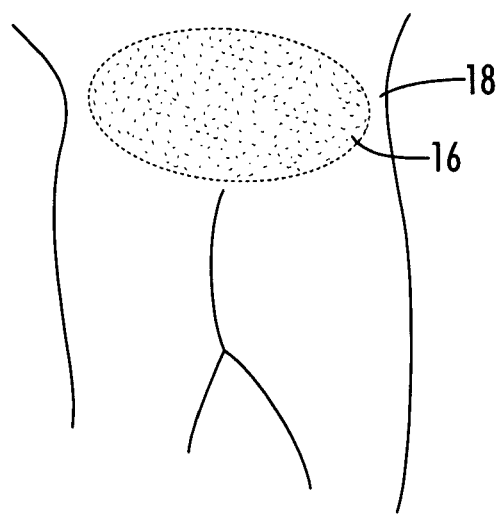
FIG. 3 is an example of a skin area prior to interaction between the solution and skin before the solution reacts to any temperature variances on the skin.
Figure 4:
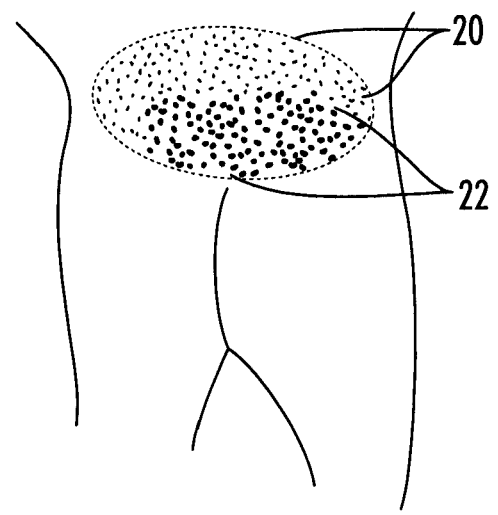
FIG. 4 is an example of the solution reacting to the temperature variance wherein darker areas of the skin are hotter than the lighter areas.

FIGS. 3 and 4 show an example of a before and after adjustment of the solution as placed on the skin in accordance with the current disclosure. FIG. 3 shows the solution 16 as applied to the skin 18 of a patient. After a predetermined length of time, preferably approximately 1 or 2 seconds, the solution 16 can go from its original color to various colors that are shown in the color key 14. Preferably this original color is clear and/or a neutral color that approximates skin tone. As shown in FIG. 4 when the solution reacts with the temperature variance on the skin there can be mild temperature changes as indicated by the numeral 20 or large temperature changes as indicated by the numeral 22. As the color differential is observed the darker colors 22 indicate an area of risk of neurosis of the skin. From this analysis, a patient can then receive skin care protocol to stop the onset of necrosis, decubiti, and/or decubitus ulcers.

Additionally, the current method and kit can be used to diagnose other ailments or illnesses that have a symptom of increased skin temperature. For example, the current inventive method and kit could be useful for the detection, or preferably the early detection, of most any other ailment or illness that causes and increased skin temperature. The increase skin temperature can be recorded and analyzed through a realization of the color change in the solution. As a result, the skin area proximate to the color change can then be studied for potential abnormalities. For example, the current method and kit could be used to identify the potential onset of skin cancer or breast cancer when those diseases exhibit heightened skin temperatures as a symptom.

Thermochromic materials may be used in any of the following formulae: fine pigment particles (preferred), molecular materials, or micro-encapsulated materials. The thermochromic materials are available from Clark R&D Ltd., under the trade name ColorTell. ColorTell inks are formulated in water which results in their being non-toxic and odor free. The color changes range from colorless to medium temperature color change, to a maximum temperature color change. The thermochromic materials can be reactive to temperatures ranging from 5 to 338 degrees Fahrenheit. Using a solvent in the thermochromic material increases the sensitivity and definition of the change in color in response to variations in temperature. Such solvents include, but are not limited to, esters and alcohol compounds.

The thermochromic material can be mixed directly into the lotion or soap or microencapsulated. U.S. Pat. Nos. 5,198,486 (Sakata), 4,305,961 (Tsutsumi et al), 4,394,447 (Cadmus et al), and 4,515,700 (Hitzaman) identify body lotions that are suitable. U.S. Pat. Nos. 6,001,344 (Vila et al.), 5,993,793 (Simone et al.), 5,955,406 (Dubief et al.) and 5,911,981 (Dahms et al.) provide information on suitable body soaps.

The viscosity of the lotion or soap is preferably thin enough to allow for topical delivery via pump or spray. This type of application facilitates prevention of false positive readings of color changes resulting from irritating skin while applying. Two unique characteristics of the product include the sprayed application of the product onto the skin serves to avoid any unnecessary friction on the skin and the product is hypoallergenic allowing use of the product on virtually all skin types.

In application, the product is delivered via a pump or spray dispenser onto an area of skin and observed for color change. If the sprayed area of the skin includes a heightened temperature, a color change will appear. The color will change from a clear appearance to red and then to a dark blue.

As indicated in a color guide, preferably on the container housing the product, if a dark color is surrounded by a lighter color, the darker area identifies an area of skin at risk for necrosis/breakdown. Skincare protocol according the healthcare provider or facility is then implemented.

The product allows for detection of decubitus ulcers in Stage One development, or earlier, by identifying for a caregiver, skilled or unskilled, where the skin breakdown is likely/occurring.

Various forms of the product can be used for various applications. For example, the product in a mixture with plain water can be used for an initial assessment, such as upon admission, and could potentially be used over the whole body to identify previously unknown areas of necrosis/potential necrosis. A version in liquid soap form can be used routinely for bathing patients with little or no mobility to accommodate assessments contemporaneously with the bathing care step. A version in conjunction with an emollient can be used predominantly on patients with impaired mobility when they are repositioned. The emollient version can combine functions of skin assessment and application of an emollient to prevent further/future breakdown. The liquid soap and emollient versions can also provide the caregiver immediately available information about locations where tissue is more fragile should be more gently addressed while bathing/applying emollient, which adds an additional form of prevention of future breakdown.

The benefit of the product include the used for early detection of venous stasis ulcers, which, in the United States, have an estimated occurrence rate of 600,000 per year with treatment costs totaling more than a billion dollars annually. Thus, the health and economic implications are great.

A significant complication of venous stasis ulcers is osteomyelitis—infection in the bone. In severe cases, amputation of the affected body part, usually the leg, can be required. In other cases of osteomyelitis, extensive courses of intravenous antibiotics are required. Both of these treatments are costly and debilitating. The current invention could preemptively prevent the venous stasis ulcers and accompanying osteomyelitis by early detection.

This invention has other applications. For example it can be used by medical staff in the diagnosis of hypothermia for detection of frostbite, to determine the severity of frostbite, in the treatment of chemical burn victims where the total area of exposure may be unknown or undetectable to the eye, and in the diagnosis of radiation injuries to skin. Additionally, the invention can be used in the detection of tissue necrosis for patients who have a loss of sensation in their extremities, who are diabetic and/or who are diagnosed with compromised peripheral vascularity. The invention can be used as a visual cue for temperature goals used in relaxation techniques, in the diagnosis of deep vein thrombosis, or by inpatient facilities in the transfer of patients from/to another facility to document, or even photograph, results of skin assessments to record treatment states in the event of a negligence claim.

Thus, although there have been described particular embodiments of the present disclosure of a new and useful "Use of Heat Sensitive Color Changing Formula to Detect and Prevent the Onset of Decubitus Ulcers", it is not intended that such references be construed as limitations upon the scope of this disclosure except as set forth in the following claims.

What is claimed is:

1. A method of assessing the skin diagnosis of a patient, comprising:
   providing a water washable topical solution containing thermochromic material;
   applying said water washable topical solution to the skin of the patient;
   recording the color of the water washable topical solution as it appears on the skin of the patient;
   analyzing changes in the color of the water washable topical solution as affected by the skin of the patient after a period of predetermined time; and
   correlating locations of changes in color of the water washable topical solution to an increase temperature of the skin at the color change location and to the risk for the onset of decubiti.

2. The method of claim 1, wherein the thermochromic material is a plurality of liquid crystals.

3. The method of claim 1, wherein the thermochromic material is a leuco dye.

4. The method of claim 1, further including providing a color key indicating the correlation between the water washable topical solution color and ranges of temperature of the skin proximate to the water washable topical solution.

5. The method of claim 4, wherein the water washable topical solution is in a liquid form.

6. The method of claim 5, wherein the water washable topical solution can be applied as a spray.

7. The method of claim 6, wherein the period of predetermined time is less than 10 seconds.

8. The method of claim 7, wherein the period of predetermined time is less than 5 seconds.

9. A kit for the early assessment of decubitus ulcers, the kit containing;
   a water washable liquid solution including a thermochromic material and soap, the thermochromic material reacting to temperature variants to display a color change with increased temperature, the temperature variants apparent when the water washable liquid solution is in contact with human skin tissue; and
   a color key indicating the correlation between the color change and ranges of temperature of that skin area proximate to the water washable liquid solution exhibiting the color change; ranges in the color key identifying a risk for tissue necrosis.

10. The kit of claim 9, wherein the thermochromic material is a plurality of liquid crystals.

11. The kit of claim 9, wherein the thermochromic material is a leuco dye.

12. A method of assessing the risk for the onset of decubitus ulcers in the skin of a patient, comprising:
   providing a water washable topical solution having a first color and containing thermochromic material, the water washable topical solution absorbable through the skin of the patient;
   applying the water washable topical solution to the skin of the patient;
   recording the color of the water washable topical solution as adjusted by variances in the temperature of the skin;
   analyzing changes in the color of the water washable topical solution as affected by the skin of the patient after a period of predetermined time;
   providing a color key indicating the correlation between the water washable topical solution color and ranges of temperature of the skin proximate to the water washable topical solution; and
   correlating locations of changes in color of the water washable topical solution to an increase temperature of the skin at the color change location and to the risk for the onset of decubiti.

13. The method of claim 12, wherein the thermochromic material is a leuco dye.

14. The method of claim 12, wherein the water washable topical solution is in a liquid form.

15. The method of claim 14, wherein the water washable topical solution can be apply as a spray.

16. The method of claim 12, wherein the period of predetermined time is less than 10 seconds.

17. The method of claim 12, wherein the period of predetermined time is less than 5 seconds.

* * * * *